US006638545B1

(12) United States Patent
Rombi

(10) Patent No.: US 6,638,545 B1
(45) Date of Patent: Oct. 28, 2003

(54) FOOD COMPLEMENT AND METHOD FOR COSMETIC TREATMENT BASED ON A GRAPE EXTRACT RICH IN POLYPHENOLS

(75) Inventor: Max Rombi, Bordighera (IT)

(73) Assignee: Laboratories Pharmascience, Carros (FR)

( * ) Notice: Subject to any disclaimer, the term of this patent is extended or adjusted under 35 U.S.C. 154(b) by 0 days.

(21) Appl. No.: 09/936,304

(22) PCT Filed: Mar. 13, 2000

(86) PCT No.: PCT/FR00/00485

§ 371 (c)(1),
(2), (4) Date: Nov. 26, 2001

(87) PCT Pub. No.: WO00/54610

PCT Pub. Date: Sep. 21, 2000

(30) Foreign Application Priority Data

Mar. 12, 1999 (FR) .......................................... 99 03076

(51) Int. Cl.⁷ .............................................. A61K 35/78
(52) U.S. Cl. ....................... 424/766; 424/725; 424/776; 424/777
(58) Field of Search ................. 424/725, 766, 424/776, 777

(56) References Cited

U.S. PATENT DOCUMENTS 4,834,998 A * 5/1989 Shrikhande

FOREIGN PATENT DOCUMENTS

| AU | 648754 B | 5/1994 |
| EP | 0 815 857 A1 * | 1/1998 |
| FR | 2659556 A1 | 9/1991 |
| WO | 90/13304 A1 | 11/1990 |
| WO | 90 13304 | 11/1990 |

OTHER PUBLICATIONS

Database WPI, Section Ch, Week 199545, Derwent Publications Ltd., Long, GB & CN1 094 901A, Nov. 16, 1994 XP002125460 Abstract Only.

Database WPI, Acc. No. 1995–345078/199545, Derwent Publications Ltd., Great Britain, patent family search and abstract for CN 1094901A, published Nov. 16, 1994.

* cited by examiner

Primary Examiner—Leon B. Lankford, Jr.
Assistant Examiner—Ruth A Davis
(74) Attorney, Agent, or Firm—Burns, Doane, Swecker & Mathis, L.L.P.

(57) ABSTRACT

The invention concerns firstly a food complement for dietetic and/or cosmetic purposes, containing anti-lipase properties, for oral administration. Said food complement is characterised in that it comprises a grape extract rich in or enriched with polyphenols.

16 Claims, No Drawings

FOOD COMPLEMENT AND METHOD FOR COSMETIC TREATMENT BASED ON A GRAPE EXTRACT RICH IN POLYPHENOLS

The present invention relates to the general field of dietetic and/or cosmetic food supplements. The invention is also directed toward a cosmetic treatment process and in particular an action against cellulite. The invention thus relates firstly to the very general field of treating obesity.

The therapeutic objective as regards obesity is well defined: it is a matter either of allowing the individual to lose a significant amount of weight, or of helping the individual to maintain the lowest desirable weight level.

Several types of approach have been envisaged to date.

Nutritional approaches are directed toward reducing the energy supply in the form of foods. This may be achieved by drastically reducing the energy supplies or by replacing high-energy nutrients with others that are lower in energy: such as indigestible replacement fats, structured triglycerides with reduced assimilation or non-assimilable dietary fiber.

Therapeutic approaches may have various targets.

Reducing the food intake may be the first objective. Reducing the food intake may be attempted by the use of anorexigenic substances, the short-term effects of which are shown, but the duration of use of which is limited on account of adverse side effects. Specifically, very few of these products can truly by used and their long-term efficacy remains a matter of considerable discussion. New molecules are under evaluation or may reach this stage in the near future, but their value still remains to be shown.

A second objective may be to increase the energy expenditure by using heat-generating substances acting at the central or peripheral level. The use of these substances still remains limited.

A third objective is to reduce the assimilation of dietary fats, or even possibly that of carbohydrates. This is a more recent approach which is gaining in interest. Reducing the assimilation of dietary fats may be obtained either by reducing the activity of the digestive enzymes concerned, or by modifying the properties of the interfaces transporting the lipid molecules, emulsions, vesicles or micelles.

The present invention relates firstly to a dietetic and/or cosmetic food supplement with antilipase properties for oral administration. This food supplement is characterized in that it comprises a grape extract which is rich or enriched in polyphenols.

According to one particular characteristic of the present invention, the food supplement advantageously comprises from 30% to 90% by weight of polyphenols.

According to another characteristic of the invention, the food supplement contains from 10% to 60% by weight of proanthocyanidols.

According to another characteristic of the invention, the food supplement contains from 0.001% to 0.1% by weight of trans-resveratrol.

The grape extracts used in accordance with the present invention may be obtained either from grape marc or from grape pips and/or from grape seed shells and/or optionally from grape stalks.

In general, the grape extracts contain polyphenols and in particular proanthocyanidols and anthocyanosides.

In accordance with the present invention, the food supplements have a rich or enriched polyphenol content.

Polyphenols extracted from grapes have multiple biological activities:

- proanthocyanidols may be considered as powerful free-radical scavengers which would halt the oxidation of the LDLs responsible for the formation of atheroma plaques.
- the action of procyanidol oligomers (PCO) on vascular walls, demonstrated in animals and confirmed in man, is reflected by an increase in the resistance of the blood capillaries and by a reduction in their permeability.
- polyphenols protect fibrous proteins, in particular collagen and elastin, against enzymatic degradation.
- polyphenols also lead to a reduction in the cholesterol level in the blood, and
- they have anti-platelet-clotting activity.

Other actions have also been envisaged, and in particular an action of polyphenols as antiinflammatory agents, vascular protective agents, anticaries agents, antihistamine agents, anticarcinogenic agents or antisun agents.

Non-flavonoid polyphenol derivatives, among which is resveratrol, are also thought to have antioxidant qualities and might play an antiviral, anticarcinogenic and immuno-regulatory role.

In the context of the present invention, the grape extracts present in the food supplements are rich or enriched in polyphenols, to give them inhibitory activity on digestive lipases.

A study has made it possible to demonstrate that a grape extract in accordance with the present invention, at a dose of 6 mg per 100 mg of lipids, entirely eliminates the emulsification of fats in the stomach.

On the other hand, in the duodenum, such an extract significantly reduces, by about 16%, the emulsification of fats without totally eliminating it. Given that the emulsification of fats is the step which is essential to the action of lipases on dietary fats, these results demonstrate the capacity for mechanical and thus reversible inhibition of the digestive lipases, which is preferable to a chemical inhibition which may be irreversible.

Another in vitro study, performed under conditions reproducing the physiological conditions, i.e. successive action of gastric lipase and then of pancreatic lipase on triolein, demonstrated that the grape extract according to the invention, at a dose of 6 mg/100 mg of fats, allows a virtually total inhibition of gastric lipase (78% inhibition) and of pancreatic lipase (52% inhibition), i.e. a total lipolysis inhibition of close to 60%.

In the context of the present invention, research has been carried out to study the effect of grape extract on thermogenesis. This research was performed using an ex vivo pharmacological model, the principle of which is to measure the oxygen consumption of a sample of rat brown adipose tissue; the oxygen consumption is proportional to the thermogenesis induced in the brown adipose tissue by the test extract.

| Concentration of grape extract in the medium (mg/100 ml) | Oxygen consumption (millimol of oxygen/mg) |
| --- | --- |
| 0 | 43 |
| 20 | 90 |
| 40 | 136 |
| 60 | 156 |

It is found that this extract induces a large increase (110%) in thermogenesis at and above the lowest concentration.

One particular non-limiting embodiment for obtaining a grape extract which may be used in the context of the present invention will be indicated below by way of example.

The starting material (marc and/or pips) contains from 0.1% to 5% of PCO and from 0.0001 to 0.005% of trans-resveratrol.

In order to obtain an inhibition of lipases with a reasonable posology, it is necessary to have available an extract which supplies the necessary doses of polyphenols in a small volume. By way of example, the following extraction process may be used: 1 kg of marc (or pips) is extracted with 5 kg of 60% ethanol (V/V). After filtration, the extract is concentrated under partial vacuum at a maximum temperature of 80° C. A concentrated extract is then dried under vacuum (maximum temperature of 80° C.) or by spraying (at 200° C. maximum) with or without maltodextrin, depending on the tracer specifications selected. The dry extract thus obtained has a PCO content of between 10% and 40% PCO and between 0.001% and 0.05% of trans-resveratrol depending on the content of these components in the plant starting material.

This example of implementation of a process for such extracts is not limiting; hence, it is possible to use other solvents, in particular methanol, and optionally an antioxidant (ascorbic acid, sodium metabisulfite, etc.) to prevent oxidation of the polyphenols.

Such a concentrated extract may, where appropriate, undergo a second extraction, in particular with ethyl acetate, to obtain a dry extract with a PCO content of greater than 50%.

The PCO content may be determined, for example, by using the following analytical method. The starting material to be analyzed is extracted with a water/acetone mixture (10/30 V/V). After dilution, the extraction solution is loaded onto a cartridge containing the C18 reverse-phase stationary phase. After rinsing, the PCOs are eluted with ethyl acetate. The purified solution is assayed by colorimetry with the sulfuric vanillin reagent against a catechin control.

The present invention also covers a cosmetic treatment process, and in particular a process for combating cellulite, which involves the oral administration of from 0.2 to 2 grams per day of the grape extract rich or enriched in polyphenols as described above, and forming part of the composition of the above food supplement.

The invention thus also relates to a food supplement packaged in a unit dosage form intended for a daily usage dose of from 0.2 to 2 grams of said grape extract.

What is claimed is:

1. A method for the treatment of cellulite, obesity or excess weight comprising orally administering to a patient in need of such treatment a food supplement comprising an effective amount of a grape extract, said extract being rich or enriched in polyphenols and having a proportion of from 30% to 90% by weight of polyphenols and from 0.001% to 0.1% by weight of trans-resveratrol.

2. The method as claimed in claim 1, wherein said extract is obtained from grape marc.

3. The method as claimed in claim 1, wherein the extract is obtained from grape pips and/or grape seed shells.

4. The method as claimed in claim 1, wherein said extract is administered at a daily dose of from 0.2 to 2 grams.

5. A method for the treatment of cellulite, obesity or excess weight comprising orally administering to a patient in need of such treatment a food supplement comprising an effective amount of a grape extract, said extract being rich or enriched in polyphenols and having a proportion of from 30% to 90% by weight of polyphenols, from 10% to 60% by weight of proanthocyanidols and from 0.001% to 0.1% by weight of trans-resveratrol.

6. The method as claimed in claim 5, wherein said extract is obtained from grape marc.

7. The method as claimed in claim 5, wherein the extract is obtained from grape pips and/or grape seed shells.

8. The method as claimed in claim 5, wherein said extract is administered at a daily dose of from 0.2 to 2 grams.

9. A method for the treatment of cellulite comprising orally administering to a patient in need of such treatment a food supplement comprising an effective amount of a grape extract, said extract being rich or enriched in polyphenols and having a proportion of from 30% to 90% by weight of polyphenols and from 0.001% to 0.1% by weight of trans-resveratrol.

10. The method as claimed in claim 9, wherein said extract is obtained from grape marc.

11. The method as claimed in claim 9, wherein said extract is obtained from grape pips and/or grape seed shells.

12. The method as claimed in claim 9, wherein said extract is administered at a daily dose of from 0.2 to 2 grams.

13. A method for the treatment of cellulite comprising orally administering to a patient in need of such treatment a food supplement comprising an effective amount of a grape extract, said extract being rich or enriched in polyphenols and having a proportion of from 30% to 90% by weight of polyphenols, from 10% to 60% by weight of proanthocyanidols and from 0.001% to 0.1% by weight of trans-resveratrol.

14. The method as claimed in claim 13, wherein said extract is obtained from grape marc.

15. The method as claimed in claim 13, wherein said extract is obtained from grape pips and/or grape seed shells.

16. The method as claimed in claim 13, wherein said extract is administered at a daily dose of from 0.2 to 2 grams.

* * * * *